(12) United States Patent
Collier et al.

(10) Patent No.: US 10,251,828 B2
(45) Date of Patent: *Apr. 9, 2019

(54) COSMETIC COMPOSITION AND METHODS OF USE THEREOF

(71) Applicant: Mary Kay Inc., Addison, TX (US)

(72) Inventors: Julia Collier, Addison, TX (US); Michael Frushour, Dallas, TX (US); Kim Wilson, Aledo, TX (US)

(73) Assignee: Mary Kay Inc., Addison, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/169,613

(22) Filed: Oct. 24, 2018

(65) Prior Publication Data

US 2019/0053996 A1    Feb. 21, 2019

Related U.S. Application Data

(63) Continuation of application No. 15/532,411, filed as application No. PCT/US2015/063757 on Dec. 3, 2015, now Pat. No. 10,137,074.

(60) Provisional application No. 62/086,808, filed on Dec. 3, 2014.

(51) Int. Cl.
| | | |
|---|---|---|
| *A61K 8/73* | (2006.01) | |
| *A61K 8/49* | (2006.01) | |
| *A61K 8/362* | (2006.01) | |
| *A61Q 19/00* | (2006.01) | |
| *A61K 8/92* | (2006.01) | |
| *A61K 8/37* | (2006.01) | |
| *A61K 8/39* | (2006.01) | |
| *A61K 8/29* | (2006.01) | |

(52) U.S. Cl.
CPC ............... *A61K 8/731* (2013.01); *A61K 8/29* (2013.01); *A61K 8/362* (2013.01); *A61K 8/37* (2013.01); *A61K 8/375* (2013.01); *A61K 8/39* (2013.01); *A61K 8/494* (2013.01); *A61K 8/922* (2013.01); *A61Q 19/00* (2013.01); *A61Q 19/005* (2013.01); *A61Q 19/007* (2013.01); *A61K 2800/10* (2013.01)

(58) Field of Classification Search
CPC ........ A61K 8/731; A61K 8/494; A61K 8/362; A61K 8/922; A61K 8/375; A61K 8/39; A61K 8/37; A61K 8/29; A61K 2800/10; A61Q 19/007; A61Q 19/005; A61Q 19/00
See application file for complete search history.

(56) References Cited

U.S. PATENT DOCUMENTS

| | | |
|---|---|---|
| 4,883,659 A | 11/1989 | Goodman et al. |
| 5,082,660 A | 1/1992 | Ounanian et al. |
| 6,924,256 B2 | 8/2005 | Massaro et al. |
| 2007/0275021 A1 | 11/2007 | Lee et al. |
| 2013/0209504 A1 | 8/2013 | Florence et al. |

FOREIGN PATENT DOCUMENTS

| | | |
|---|---|---|
| CN | 103349623 | 10/2013 |
| KR | 1019990022593 | 1/2001 |
| KR | 1020030063708 | 3/2005 |
| KR | 1020040096201 | 5/2006 |
| WO | WO 1994/018292 | 8/1994 |
| WO | WO 2009/085472 | 7/2009 |
| WO | WO 2014/081939 | 5/2014 |

OTHER PUBLICATIONS

International Search Report and Written Opinion issued in International Patent Application No. PCT/US2015/063757, dated Mar. 22, 2016.

*Primary Examiner* — Trevor Love
(74) *Attorney, Agent, or Firm* — Norton Rose Fulbright US LLP

(57) ABSTRACT

Disclosed is an anhydrous lip moisturizing composition and a method of use for moisturizing lips. The composition can include 20% to 30% by weight of caprylic/capric triglyceride; 12% to 22% by weight of tridecyl trimellitate; 1% to 15% by weight of jojoba esters; 5% to 10% by weight of *Helianthus annus* (sunflower) seed oil; 2% to 10% by weight of microcrystalline wax; and 2% to 10% by weight of beeswax.

3 Claims, No Drawings

COSMETIC COMPOSITION AND METHODS OF USE THEREOF

CROSS-REFERENCE TO RELATED APPLICATIONS

This application is a continuation of U.S. patent application Ser. No. 15/532,411, filed Jun. 1, 2017, which is a national phase under 35 U.S.C. § 371 of International Application No. PCT/US2015/063757, filed Dec. 3, 2015, which claims priority to U.S. Provisional Patent Application Ser. No. 62/086,808, filed Dec. 3, 2014. The contents of each of the referenced applications are incorporated into the present application by reference.

BACKGROUND OF THE INVENTION

1. Field of the Invention

The present invention relates generally to the field of cosmetics. More particularly, it concerns compositions that can be used to exfoliate, moisturize, or prepare skin for moisturization. In another aspect, the composition can be used as a cleanser to remove dirt, oil, grease, tars, etc. from surfaces.

2. Description of Related Art

Several skin moisturizing and/or exfoliating compositions are currently available. These compositions have various drawbacks ranging from unpleasant tactile properties (e.g., heavy, greasy, or sticky feel), instability issues, skin-irritation issues, insufficient moisturization capabilities, or the compositions are too harsh for sensitive skin such as the lips.

Further, cleansing compositions oftentimes have ingredients that can be caustic to the surfaces to be cleansed. For instance, many types of cleansers use certain surfactants, which can cause skin irritation.

SUMMARY OF THE INVENTION

The present invention overcomes deficiencies in the art by providing compositions and methods of use that are designed to exfoliate dead surface skin cells from skin on the body and lips. The compositions can also moisturize skin, prepare skin for moisturization, and cleanse skin and/or other objects (e.g., articles of manufacture).

In one aspect disclosed herein are compositions capable of exfoliating skin, moisturizing skin, preparing skin for moisturization, cleansing skin, and/or cleansing a surface. In this regard, there is disclosed compositions that include any one of, any combination of, or all of water, glyceryl stearate, cetyl alcohol, sorbitol, titanium dioxide, hydroxyethylcellulose, methylparaben, DMDM hydantoin, and disodium EDTA. The amounts of the ingredients within the composition can vary (e.g., amounts can be as low as 0.000001% to as high as 85% w/w or any range therein). In one instance, the composition includes 25% to 80% w/w of water, 1% to 15% w/w of glyceryl stearate, 0.5% to 10% w/w of cetyl alcohol, 0.1% to 3% w/w of sorbitol, 0.1% to 1.5% w/w of titanium dioxide, 0.1% to 1.5% w/w of hydroxyethylcellulose, 0.05% to 1% w/w of methylparaben, 0.01% to 0.5% w/w of DMDM hydantoin, and 0.01% to 0.5% w/w of disodium EDTA. In another instance the composition further comprises polyethylene beads and/or hydrated silica particles. In yet another instance the composition may further comprise a fragrance agent, aroma agent, and/or flavoring agent. In one instance, the composition may comprise 0.01% to 1.5% w/w of a fragrance agent, aroma agent, and/or flavoring agent. In another instance, the compositions above are capable of exfoliating skin. In yet another instance, the compositions above are capable of moisturizing skin. In one instance, the compositions above are capable of cleansing a surface. In one instance, the compositions above are capable of cleansing a skin surface.

In another aspect disclosed herein, the compositions above further include any one of, any combination of, or all of bentonite, stearic acid, PEG-100 stearate, glycerin, hydrogenate polyisobutene, PVP, petrolatum, cetyl esters, stearyl alcohol, triethanolamine, magnesium aluminum silicate, butylene glycol, and tocopheryl acetate. The amounts of the ingredients within the composition can vary (e.g., amounts can be as low as 0.000001% to as high as 85% w/w or any range therein). In one instance, the composition includes 1% to 15% w/w of bentonite, 0.5% to 5% w/w of stearic acid, 0.5% to 5% w/w of PEG-100 stearate, 0.5% to 5% w/w of glycerin, 0.1% to 3% w/w of hydrogenate polyisobutene, 0.1% to 3% w/w of PVP, 0.1% to 3% w/w of petrolatum, 0.1% to 3% w/w of cetyl esters, 0.1% to 3% w/w of stearyl alcohol, 0.1% to 1.5% w/w of triethanolamine, 0.1% to 1.5% w/w of magnesium aluminum silicate, 0.05% to 1% w/w of butylene glycol, and 0.01% to 1% w/w of tocopheryl acetate. In another instance, the compositions above are capable of exfoliating the skin of lips. In yet another instance, the compositions above are capable of moisturizing the skin of lips. In one instance, the compositions above are capable of cleansing the skin of lips.

In yet another aspect disclosed herein, the compositions above are topical masks.

In one aspect, the compositions above which include any one of, any combination of, or all of water, glyceryl stearate, cetyl alcohol, sorbitol, titanium dioxide, hydroxyethylcellulose, methylparaben, DMDM hydantoin, disodium EDTA, polyethylene beads, hydrated silica particles, fragrance agent, aroma agent, and/or flavoring agents further comprise disodium cocoamphodiacetate, PPG-5-ceteth-10 phosphate, sodium laureth sulfate, cocamidopropyl hydroxysultaine, citric acid, and sodium chloride. In one instance, the composition comprise 5% to 20% w/w of disodium cocoamphodiacetate, 0.5% to 5% w/w of PPG-5-ceteth-10 phosphate, 0.5% to 5% w/w of sodium laureth sulfate, 0.1% to 3% w/w of cocamidopropyl hydroxysultaine, 0.1% to 1.5% w/w of citric acid, and 0.1% to 1% w/w of sodium chloride. In another instance, the composition is a cream.

In a further aspect, there is disclosed a cosmetic composition comprising: sucrose; *Butyrospermum parkii* (shea) butter; and a dermatologically acceptable vehicle. In some embodiments, the composition comprises 35 to 45% by weight of sucrose and 7 to 15% by weight of *Butyrospermum parkii* (shea) butter. In some embodiments, the composition further comprises tridecyl trimellitate; glycerin; *Helianthus annus* (sunflower) seed oil; caprylic/capric triglyceride; trihydroxystearin; and glyceryl stearate. In some embodiments, the composition comprises 13 to 20% by weight of tridecyl trimellitate; 2 to 12% by weight of glycerin; 2 to 12% by weight of *Helianthus annus* (sunflower) seed oil; 2 to 12% by weight of caprylic/capric triglyceride; 1 to 6% by weight of trihydroxystearin; and 0.5 to 5% by weight of glyceryl stearate. In some embodiments, the composition is an emulsion, a lotion, a gel, or an ointment. In some embodiments, the composition is an emulsion. In some embodiments, the composition is formulated with a dermatologically acceptable vehicle as described herein. In some embodiments, the sucrose is granulated. In some embodiments, the sucrose does not contain esters. In some embodiments, the cosmetic composition further comprise one or more additional ingredients selected from one or more moisturizing agents, thickening agents, emulsifiers, flavoring agents, absorbents, antioxidants, opacifying agents, solvents, and pH adjusters. In some embodiments, the composition comprises one or more additional ingredients described herein.

Further aspects relate to a method of exfoliating lips comprising applying a composition of the disclosure to the lips followed by rinsing said composition from the lips within 10 minutes after application. In some embodiments, the composition removes dead skin and/or residual food or beverage particles.

Further aspects of the disclosure relate to a moisturizing cosmetic composition comprising: microcrystalline wax; beeswax; *Butyrospermum parkii* (shea) butter; *Mangifera indica* (mango) seed butter; and a dermatologically acceptable vehicle. In some embodiments, the moisturizing cosmetic composition comprises 2 to 10% by weight of microcrystalline wax; 2 to 10% by weight of beeswax; 0.5 to 12% by weight of *Butyrospermum parkii* (shea) butter; and 0.5 to 12% by weight of *Mangifera indica* (mango) seed butter. In some embodiments, the moisturizing cosmetic composition further comprises caprylic/capric triglyceride; tridecyl trimellitate; jojoba esters; *Helianthus annus* (sunflower) seed oil; glyceryl stearate; cetyl alcohol; and pentaerythrityl tetraisostearate. In some embodiments, the moisturizing cosmetic composition comprises 20 to 30% by weight of caprylic/capric triglyceride; 12 to 22% by weight of tridecyl trimellitate; 1 to 15% by weight of jojoba esters; 5 to 10% by weight of *Helianthus annus* (sunflower) seed oil; 2 to 8% by weight of glyceryl stearate; 2 to 8% by weight of cetyl alcohol; and 2 to 8% by weight of pentaerythrityl tetraisostearate. In some embodiments, the moisturizing cosmetic composition is an emulsion, a lotion, a gel, a cream, or an ointment. In some embodiments, the moisturizing cosmetic composition is a cream. In some embodiments, the moisturizing cosmetic composition is formulated with a dermatologically acceptable vehicle as described herein. In some embodiments, the moisturizing cosmetic composition is homogenous. In some embodiments, the moisturizing cosmetic composition further comprises one or more additional ingredients selected from one or more absorbants, flavoring agents, opacifying agents, and antioxidants. In some embodiments, the moisturizing cosmetic composition comprises one or more additional ingredients described herein.

Further aspects of the disclosure relate to a method of moisturizing lips comprising applying a moisturizing cosmetic composition described herein to the lips.

Further aspects relate to a method for exfoliating and moisturizing lips comprising the steps of: applying a cosmetic composition of the disclosure to the lips followed by rinsing said composition from the lips within 10 minutes after application; and applying a moisturizing cosmetic composition of the disclosure to the lips. In some embodiments, the steps are performed in a specific order. In some embodiments, the cosmetic composition is applied before the moisturizing cosmetic composition.

Further aspects relate to a composition comprising: a solvent; isodecane; caprylic/capric triglyceride, dimethicone, cetyl alcohol, stearic acid, arachidyl alcohol, hydroxyethyl acrylate/sodium acryloyldimethyl taurate copolymer, behenyl alcohol, isohexadecane, arachidyl glucoside, acrylates/$C_{10-30}$ alkyl acrylate crosspolymer, polysorbate 60; and a dermatologically acceptable vehicle. In some embodiments, the composition comprises 60 to 85% by weight of a solvent, 4 to 10% by weight of isodecane, 0.5 to 4% by weight of caprylic/capric triglyceride, 0.2 to 3% by weight of dimethicone, 0.2 to 3% by weight of cetyl alcohol, 0.2 to 3% by weight of stearic acid, 0.1 to 2% by weight of arachidyl alcohol, 0.05 to 2% by weight of hydroxyethyl acrylate/sodium acryloyldimethyl taurate copolymer, 0.05 to 2% by weight of behenyl alcohol, 0.05 to 2% by weight of isohexadecane, 0.01 to 1% by weight of arachidyl glucoside, and 0.01 to 1% by weight of acrylates/C10-30 alkyl acrylate crosspolymer, polysorbate 60. In some embodiments, the composition is formulated with a dermatological vehicle described herein. In some embodiments, the composition is an emulsion, a lotion, a gel, or an ointment. In some embodiments, the composition is a lotion. In some embodiments, the solvent comprises water, propanediol, or both. In some embodiments, the composition further comprises one or more additional ingredients selected from one or more moisturizing agents, fragrances, preservatives, conditioning agents, pH adjusters, chelating agents, and emulsifiers.

In another aspect, the compositions above are capable of being removed before a moisturizer is applied to the surface to which the composition was applied.

Also disclosed is a method of exfoliating skin comprising topically applying any one of the compositions disclosed herein to skin. The skin to be exfoliated may be non-sensitive or sensitive skin. In some embodiments, the sensitive skin is the skin of lips.

In another aspect, a method is disclosed of moisturizing skin comprising topically applying any one of the compositions disclosed herein to skin. In one instance, disclosed is a method of moisturizing skin comprising topically applying any one of the compositions disclosed herein to skin, removing the composition from the skin, and topically applying a moisturizer to the skin from which the composition was removed. The composition can be applied to dry skin, flaky skin, chapped skin, cracked skin, etc.

Even further, in another aspect, a method is disclosed of cleansing a surface comprising applying any one of the compositions disclosed herein to a surface. In yet another aspect, the method of cleansing a surface may further comprise removing said composition from the surface. Moreover, in another aspect, disclosed is a method of cleansing a skin surface comprising applying any one of the compositions disclosed herein to a skin surface.

In yet another aspect, a method is disclosed of any of the previous methods further comprising applying the composition to skin of a lip.

The compositions herein can remain on the surface or skin for a period of time, or be rinsed with water, alcohol, oil, etc. or peeled from the surface or skin. The composition can be applied to a surface or skin having dirt, oil, sebum, tar, or grease on said surface or skin, with the result being that said dirt, oil, tar, sebum, or grease is removed from said surface or skin.

The compositions disclosed throughout this specification can be used on a surface, on lip skin, on facial skin, and/or on body skin (e.g., hands, arms, chest, abdomen, upper and lower back, legs, buttocks, feet, etc.).

In particular aspects, the compositions disclosed herein are formulated as a topical skin composition. The composition can have a dermatologically acceptable vehicle or carrier for the compounds, compositions and extracts. The composition can further include a moisturizing agent or a humectant, a surfactant, a silicone containing compounds, a UV agent, an oil, and/or other ingredients identified in this specification or those known in the art. The composition can be a lotion, cream, gel, serum, emulsion (e.g., oil-in-water, water-in-oil, silicone-in-water, water-in-silicone, water-in-oil-in-water, oil-in-water-in-oil, oil-in-water-in-silicone, etc.), solutions (e.g., aqueous or hydro-alcoholic solutions), anhydrous bases (e.g., lipstick or a powder), ointments, milk, paste, aerosol, solid forms, eye jellies, etc. The composition can be in powdered form (e.g., dried, lyophilized, particulate, etc.). The composition can be formulated for topical skin application at least 1, 2, 3, 4, 5, 6, 7, or more times a day during use. In other aspects disclosed herein, compositions can be storage stable or color stable, or both. It is also contemplated that the viscosity of the composition can be selected to achieve a desired result, e.g., depending on the type of composition desired, the viscosity of such composition can be from about 1 cps to well over 1 million cps or any range or integer derivable therein (e.g., 2 cps, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 10000000, cps, etc., as measured on a Brookfield Viscometer using a TC spindle at 2.5 rpm at 25° C.).

The compositions disclosed herein can also be modified to have a desired oxygen radical absorbance capacity (ORAC) value. In certain non-limiting aspects, the compositions disclosed herein or the component or extracts thereof identified throughout this specification can be modified to have an ORAC value per mg of at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 70, 80, 90, 95, 100, 200, 300, 400, 500, 600, 700, 800, 900, 1000, 2000, 3000, 4000, 5000, 6000, 7000, 8000, 9000, 10000, 15000, 20000, 30000, 50000, 100000 or more or any range derivable therein.

The compositions in non-limiting aspects can have a pH of about 6 to about 9. In other aspects, the pH can be 1, 2, 3, 4, 5, 6, 7, 8, 9, 10, 11, 12, 13, or 14. The compositions can include a triglyceride. Non-limiting examples include small, medium, and large chain triglycerides. In certain aspects, the triglyceride is a medium chain triglyceride (e.g., caprylic capric triglyceride). The compositions can also include preservatives. Non-limiting examples of preservatives include methylparaben, propylparaben, or a mixture of methylparaben and propylparaben.

Compositions disclosed herein can have UVA and UVB absorption properties. The compositions can have an sun protection factor (SPF) of 2, 3, 4, 5, 6, 7, 8, 9, 10, 11, 12, 13, 14, 15, 20, 25, 30, 35, 40, 45, 50, 55, 60, or more, or any integer or derivative therein. The compositions can be sunscreen lotions, sprays, or creams.

The compositions disclosed herein can also include any one of, any combination of, or all of the following additional ingredients: water, a chelating agent, a moisturizing agent, a preservative, a thickening agent, a silicone containing compound, an essential oil, a structuring agent, a vitamin, a pharmaceutical ingredient, or an antioxidant, or any combination of such ingredients or mixtures of such ingredients. In certain aspects, the composition can include at least two, three, four, five, six, seven, eight, nine, ten, or all of these additional ingredients identified in the previous sentence. Non-limiting examples of these additional ingredients are identified throughout this specification and are incorporated into this section by reference. The amounts of such ingredients can range from 0.0001% to 99.9% by weight or volume of the composition, or any integer or range in between as disclosed in other sections of this specification, which are incorporated into this paragraph by reference.

Also disclosed herein are Embodiments one to twenty-seven. Embodiment one is a composition comprising: water; glyceryl stearate; cetyl alcohol; sorbitol; titanium dioxide; hydroxyethylcellulose; methylparaben; DMDM hydantoin; and disodium EDTA. Embodiment two is the composition of Embodiment one, comprising 25% to 80% w/w of water; 1% to 15% w/w of glyceryl stearate; 0.5% to 10% w/w of cetyl alcohol; 0.1% to 3% w/w of sorbitol; 0.1% to 1.5% w/w of titanium dioxide; 0.1% to 1.5% w/w of hydroxyethylcellulose; 0.05% to 1% w/w of methylparaben; 0.01% to 0.5% w/w of DMDM hydantoin; and 0.01% to 0.5% w/w of disodium EDTA. Embodiment three is the composition of any of Embodiments one or two, further comprising polyethylene beads or hydrated silica particles. Embodiment four is the composition of Embodiment three, wherein the composition comprises hydrated silica particles. Embodiment five is the composition of any of Embodiments one through four, further comprising one or more additional ingredients selected from one or more of a fragrance agent, aroma agent, and flavoring agent. Embodiment six is the composition of Embodiment five, comprising 0.01% to 1.5% w/w of one or more additional ingredients selected from one or more of a fragrance agent, aroma agent, and flavoring agent. Embodiment seven is the composition of any of Embodiments one through six, wherein the composition is capable of exfoliating skin. Embodiment eight is the composition of any of Embodiments one through six, wherein the composition is capable of moisturizing skin. Embodiment nine is the composition of any of Embodiments one through six, wherein the composition is capable of cleansing a surface. Embodiment ten is the composition of Embodiment nine, wherein the surface is a skin surface. Embodiment eleven is the composition of any of Embodiments one through ten, further comprising: bentonite; stearic acid; PEG-100 stearate; glycerin; hydrogenate polyisobutene; PVP; petrolatum; cetyl esters; stearyl alcohol; triethanolamine; magnesium aluminum silicate; butylene glycol; and tocopheryl acetate. Embodiment twelve is the composition of Embodiment eleven, comprising 1% to 15% w/w of bentonite; 0.5% to 5% w/w of stearic acid; 0.5% to 5% w/w of PEG-100 stearate; 0.5% to 5% w/w of glycerin; 0.1% to 3% w/w of hydrogenate polyisobutene; 0.1% to 3% w/w of PVP; 0.1% to 3% w/w of petrolatum; 0.1% to 3% w/w of cetyl esters; 0.1% to 3% w/w of stearyl alcohol; 0.1% to 1.5% w/w of triethanolamine; 0.1% to 1.5% w/w of magnesium aluminum silicate; 0.05% to 1% w/w of butylene glycol; and 0.01% to 1% w/w of tocopheryl acetate. Embodiment thirteen is the composition of Embodiment eleven, wherein the composition is capable of exfoliating skin of lips. Embodiment fourteen is the composition of Embodiment eleven, wherein the composition is capable of moisturizing skin of lips. Embodiment fifteen is the composition of Embodiment eleven, wherein the composition is capable of cleansing skin of lips. Embodiment sixteen is the composition of any of Embodiments one through fifteen, wherein the composition is a topical mask. Embodiment seventeen is the composition of any of Embodiments one through ten, further comprising: disodium cocoamphodiacetate; PPG-5-ceteth-10 phosphate; sodium laureth sulfate; cocamidopropyl hydroxysultaine; citric acid; and sodium chloride. Embodiment eighteen is the composition of Embodiment seventeen, comprising 5% to 20% w/w of disodium cocoamphodiacetate; 0.5% to 5% w/w of PPG-5-ceteth-10 phosphate; 0.5% to 5% w/w of sodium laureth sulfate; 0.1% to 3% w/w of cocamidopropyl hydroxysultaine; 0.1% to 1.5% w/w of citric acid; and 0.1% to 1% w/w of sodium chloride. Embodiment nineteen is the composition of any of Embodiments one through fifteen and seventeen through eighteen, wherein the composition is a cream. Embodiment twenty is the composition of any of Embodiments one through nineteen, wherein the composition is capable of being removed before a moisturizer is applied to the surface to which the composition was applied. Embodiment twenty-one is a method of exfoliating skin comprising topically applying any one of the compositions of Embodiments one through twenty to skin. Embodiment twenty-two is a method of moisturizing skin comprising topically applying any one of the compositions of Embodiments one through twenty to skin. Embodiment twenty-three is a method of moisturizing skin comprising: topically applying any one of the compositions of Embodiments one through twenty to skin; removing the composition from the skin; and topically applying a moisturizer to the skin to which the composition was removed. Embodiment twenty-four is a method of cleansing a surface comprising applying any one of the compositions of Embodiments one through twenty to a surface. Embodiment twenty-five is the method of Embodiment twenty-four, further comprising removing said composition from the surface. Embodiment twenty-six is the method of any of Embodiments twenty-four or twenty-five, wherein the surface is a skin surface. Embodiment twenty-seven is a method of any of Embodiments twenty-one through twenty-six, further comprising applying the composition to skin of a lip.

Also disclosed in the context of the current disclosure are embodiments twenty-eight to thirty-seven. Embodiment twenty-eight is a cosmetic composition comprising: sucrose; *Butyrospermum parkii* (shea) butter; and a dermatologically acceptable vehicle. Embodiment twenty-nine is the cosmetic composition of embodiment twenty-eight comprising 35 to 45% by weight of sucrose and 7 to 15% by weight of *Butyrospermum parkii* (shea) butter. Embodiment thirty is the cosmetic composition of embodiment twenty-eight or twenty-nine, wherein the composition further comprises tridecyl trimellitate; glycerin; *Helianthus annus* (sunflower) seed oil; caprylic/capric triglyceride; trihydroxystearin; and glyceryl stearate. Embodiment thirty-one is the cosmetic composition of embodiment thirty, wherein the composition comprises: 13 to 20% by weight of tridecyl trimellitate; 2 to 12% by weight of glycerin; 2 to 12% by weight of *Helianthus annus* (sunflower) seed oil; 2 to 12% by weight of caprylic/capric triglyceride; 1 to 6% by weight of trihydroxystearin; and 0.5 to 5% by weight of glyceryl stearate. Embodiment thirty-two is the cosmetic composition of any one of embodiments twenty-eight to thirty-one, wherein the composition is an emulsion, a lotion, a gel, or an ointment. Embodiments thirty-three is the cosmetic composition of embodiment thirty-two, wherein the composition is an emulsion. Embodiment thirty-four is the cosmetic composition of any one of embodiments twenty-eight to thirty-three, wherein the sucrose is granulated. Embodiment thirty-five is the cosmetic composition of any one of embodiments twenty-eight to thirty-four, further comprising one or more additional ingredients selected from one or more moisturizing agents, thickening agents, emulsifiers, flavoring agents, absorbents, antioxidants, opacifying agents, solvents, and pH adjusters. Embodiment thirty-six is a method of exfoliating lips comprising applying the cosmetic composition of any one of embodiments twenty-eight to thirty-five to the lips followed by rinsing said composition from the lips within 10 minutes after application. Embodiment thirty-seven is the method of embodiment thirty-six, wherein said cosmetic composition removes dead skin and/or residual food or beverage particles.

Also disclosed in the context of the current disclosure are embodiments thirty-eight to forty-six. Embodiment thirty-eight is a moisturizing cosmetic composition comprising: microcrystalline wax; beeswax; *Butyrospermum parkii* (shea) butter; *Mangifera indica* (mango) seed butter; and a dermatologically acceptable vehicle. Embodiment thirty-nine is the moisturizing cosmetic composition of embodiment thirty-eight, wherein the composition comprises 2 to 10% by weight of microcrystalline wax; 2 to 10% by weight of beeswax; 0.5 to 12% by weight of *Butyrospermum parkii* (shea) butter; and 0.5 to 12% by weight of *Mangifera indica* (mango) seed butter. Embodiment forty is the moisturizing cosmetic composition of embodiment thirty-eight or thirty-nine, wherein the composition further comprises caprylic/capric triglyceride; tridecyl trimellitate; jojoba esters; *Helianthus annus* (sunflower) seed oil; glyceryl stearate; cetyl alcohol; and pentaerythrityl tetraisostearate. Embodiment forty-one is the cosmetic composition of embodiment forty, wherein the composition comprises: 20 to 30% by weight of caprylic/capric triglyceride; 12 to 22% by weight of tridecyl trimellitate; 1 to 15% by weight of jojoba esters; 5 to 10% by weight of *Helianthus annus* (sunflower) seed oil; 2 to 8% by weight of glyceryl stearate; 2 to 8% by weight of cetyl alcohol; and 2 to 8% by weight of pentaerythrityl tetraisostearate. Embodiment forty-two is the moisturizing cosmetic composition of any one of embodiments thirty-eight to forty-one, wherein the composition is an emulsion, a lotion, a gel, a cream, or an ointment. Embodiment forth-three is the moisturizing cosmetic composition of embodiment forty-two, wherein the composition is a cream. Embodiment forty-four is the moisturizing composition of any one of embodiments thirty-eight to forty-three, wherein the composition is homogenous. Embodiment forty-five is the moisturizing cosmetic composition of any one of embodiments thirty-eight to forty-four, further comprising one or more additional ingredients selected from one or more absorbants, flavoring agents, opacifying agents, and antioxidants. Embodiment forty-six is a method of moisturizing lips comprising applying the moisturizing cosmetic composition of any one of embodiments thirty-eight to forty-five to the lips.

Also disclosed in the context of the current disclosure is embodiment forty-seven. Embodiment forty-seven is a method for exfoliating and moisturizing lips comprising the steps of: applying the cosmetic composition of any one of embodiments one to eight to the lips followed by rinsing said composition from the lips within 10 minutes after application; and applying the moisturizing cosmetic composition of any one of embodiments thirty-eight to forty-five to the lips.

Also disclosed in the context of the current disclosure is embodiment forty-eight to fifty-four. Embodiment 48 is a composition comprising a solvent, isodecane, caprylic/capric triglyceride, dimethicone, cetyl alcohol, stearic acid, arachidyl alcohol, hydroxyethyl acrylate/sodium acryloyldimethyl taurate copolymer, behenyl alcohol, isohexadecane, arachidyl glucoside, acrylates/C10-30 alkyl acrylate crosspolymer, polysorbate 60, and a dermatologically acceptable vehicle. Embodiment forty-nine is the cosmetic composition of embodiment 48, wherein the composition comprises 60 to 85% by weight of a solvent, 4 to 10% by weight of isodecane, 0.5 to 4% by weight of caprylic/capric triglyceride, 0.2 to 3% by weight of dimethicone, 0.2 to 3% by weight of cetyl alcohol, 0.2 to 3% by weight of stearic acid, 0.1 to 2% by weight of arachidyl alcohol, 0.05 to 2% by weight of hydroxyethyl acrylate/sodium acryloyldimethyl taurate copolymer, 0.05 to 2% by weight of behenyl alcohol, 0.05 to 2% by weight of isohexadecane, 0.01 to 1% by weight of arachidyl glucoside, 0.01 to 1% by weight of acrylates/C10-30 alkyl acrylate crosspolymer, polysorbate 60. Embodiment fifty is the cosmetic composition of embodiment forty-eight or forty-nine, wherein the composition is an emulsion, a lotion, a gel, or an ointment. Embodiment fifty one is the cosmetic composition of embodiment fifty, wherein the composition is a lotion. Embodiment fifty-two is the cosmetic composition of any one of embodiments forty-eight to fifty-one, wherein the solvent comprises water, propanediol, or both. Embodiment fifty-three is the cosmetic composition of any one of embodiments forty-eight to fifty-two, further comprising one or more additional ingredients selected from one or more moisturizing agents, fragrances, preservatives, conditioning agents, pH adjusters, chelating agents, and emulsifiers. Embodiment fifty-four is a method of moisturizing skin comprising topically applying the composition of any one of embodiments forty-eight to fifty-three to skin.

Kits that include the compositions disclosed herein are also contemplated. In certain embodiments, the composition is comprised in a container. The container can be a bottle, dispenser, or package. The container can dispense a pre-determined amount of the composition. In certain aspects, the compositions is dispensed in a spray, dollop, or liquid. The container can include indicia on its surface. The indicia can be a word, an abbreviation, a picture, or a symbol.

It is also contemplated that the compositions disclosed throughout this specification can be used as a leave-on or rinse-off composition. By way of example, a leave-on composition can be one that is topically applied to skin and remains on the skin for a period of time (e.g., at least 5, 6, 7, 8, 9, 10, 20, or 30 minutes, or at least 1, 2, 3, 4, 5, 6, 7, 8, 9, 10, 11, 12, 13, 14, 15, 16, 17, 18, 19, 20, 21, 22, 23 or 24 hours, or overnight or throughout the day). Alternatively, a rinse-off composition can be a product that is intended to be applied to the skin and then removed or rinsed from the skin (e.g., with water) within a period of time such as less than 5, 4, 3, 2, or 1 minute. An example of a rinse of composition can be a skin cleanser, shampoo, conditioner, or soap. An example of a leave-on composition can be a skin moisturizer, sunscreen, mask, overnight cream, or a day cream.

It is contemplated that any embodiment discussed in this specification can be implemented with respect to any method or composition of the invention, and vice versa. Furthermore, compositions of the invention can be used to achieve methods of the invention.

In one embodiment, compositions disclosed herein can be pharmaceutically or cosmetically elegant or can have pleasant tactile properties. "Pharmaceutically elegant," "cosmetically elegant," and/or "pleasant tactile properties" describes a composition that has particular tactile properties which feel pleasant on the skin (e.g., compositions that are not too watery or greasy, compositions that have a silky texture, compositions that are non-tacky or sticky, etc.). Pharmaceutically or cosmetically elegant can also relate to the creaminess or lubricity properties of the composition or to the moisture retaining properties of the composition.

"Topical application" means to apply or spread a composition onto the surface of lips or keratinous tissue. "Topical skin composition" includes compositions suitable for topical application on lips or keratinous tissue. Such compositions are typically dermatologically-acceptable in that they do not have undue toxicity, incompatibility, instability, allergic response, and the like, when applied to lips or skin. Topical skin care compositions disclosed herein can have a selected viscosity to avoid significant dripping or pooling after application to skin.

"Keratinous tissue" includes keratin-containing layers disposed as the outermost protective covering of mammals and includes, but is not limited to, lips, skin, hair and nails.

The term "about" or "approximately" are defined as being close to as understood by one of ordinary skill in the art, and in one non-limiting embodiment the terms are defined to be within 10%, preferably within 5%, more preferably within 1%, and most preferably within 0.5%.

The term "substantially" and its variations are defined as being largely but not necessarily wholly what is specified as understood by one of ordinary skill in the art, and in one non-limiting embodiment substantially refers to ranges within 10%, within 5%, within 1%, or within 0.5%.

The terms "inhibiting" or "reducing" or any variation of these terms includes any measurable decrease or complete inhibition to achieve a desired result. The terms "promote" or "increase" or any variation of these terms includes any measurable increase or production of a protein or molecule (e.g., matrix proteins such as fibronectin, laminin, collagen, or elastin or molecules such as hyaluronic acid) to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions and methods for their use can "comprise," "consist essentially of," or "consist of" any of the ingredients or steps disclosed throughout the specification. With respect to the transitional phase "consisting essentially of," in one non-limiting aspect, a basic and novel characteristic of the compositions and methods disclosed in this specification includes the compositions' abilities to reduce or prevent symptoms associated with sensitive skin (e.g., erythema) from appearing on a user's skin.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

DESCRIPTION OF ILLUSTRATIVE EMBODIMENTS

As noted above, several of the unique aspects of the present invention are to exfoliate skin, to moisturize skin, to cleanse skin, and/or to cleanse a surface. This allows for the benefits of skin exfoliation (which can reduce the appearance of fine lines and wrinkles and even skin tone by removing unwanted spots such as melasma, hyperpigmented skin, age spots, liver spots, dark spots, and the like), moisturization, and/or cleansing on the skin of the body in general and sensitive skin such as, but not limited to, the skin of the lips.

The following subsections describe non-limiting aspects of the present invention in further detail.

In some aspects, disclosed are compositions that are designed to work as a lip mask to exfoliate sensitive skin while providing moisturization to the skin and cleansing the skin. This particular composition has a relatively high viscosity. The composition relies on a unique combination of any one of, any combination of, or all of water, glyceryl stearate, cetyl alcohol, sorbitol, titanium dioxide, hydroxyethylcellulose, methylparaben, DMDM hydantoin, disodium EDTA, hydrated silica particles, flavoring/aroma agent, bentonite, stearic acid, PEG-100 stearate, glycerin, hydrogenate polyisobutene, PVP, petrolatum, cetyl esters, stearyl alcohol, triethanolamine, magnesium aluminum silicate, butylene glycol, and tocopheryl acetate. An example of such a compound is provided in Example 1, Table 1. While hydrated silica particles may be used as an exfoliation ingredient, other exfoliation ingredients can also be used (e.g., alpha hydroxy acids, enzyme exfoliants, polyethylene beads, etc.).

In some embodiments, hydrated silica particles may be used as an exfoliants. The particles may have different shapes and sizes and may include spherical particles. One commercial source of these particles is Evonik Industries (Germany) under the trade name SIPERNAT™.

In another embodiment, the composition is designed to work as a body buffing cream to exfoliate skin while providing moisturization to the skin and cleansing the skin or a surface. The composition relies on a unique combination of any one of, any combination of, or all of water, glyceryl stearate, cetyl alcohol, sorbitol, titanium dioxide, hydroxyethylcellulose, methylparaben, DMDM hydantoin, disodium EDTA, hydrated silica particles, fragrance agent, disodium cocoamphodiacetate, PPG-5-ceteth-10 phosphate, sodium laureth sulfate, cocamidopropyl hydroxysultaine, citric acid, and sodium chloride. An example of such a compound is provided in Example 1, Table 1. While hydrated silica particles may be used as the exfoliation ingredient, other exfoliation ingredients can also be used (e.g., alpha hydroxy acids, enzyme exfoliants, polyethylene beads, etc.).

Embodiments of the compositions of the disclosure comprise a combination of ingredients such as sucrose and *Butyrospermum parkii* (shea) butter. Sucrose is a common, naturally occurring carbohydrate found in many plants and plant parts. The molecule is a disaccharide combination of the monosaccharides glucose and fructose with the formula $C_{12}H_{22}O_{11}$. When used in cosmetic compositions, sucrose (granulated sucrose in some embodiments) provides for an effective, non-toxic exfoliator. *Butyrospermum parkii* (also known as *Vitellaria paradoxa*) is commonly known as shea tree. Shea butter is composed of five principal fatty acids: palmitic, stearic, oleic, linoleic, and arachidic (see Table below). About 85 to 90% of the fatty acid composition is stearic and oleic acids. The relative proportion of these two fatty acids affects shea butter consistency. The stearic acid gives it a solid consistency, while the oleic acid influences how soft or hard the shea butter is, depending on ambient temperature. Shea butter also has phenolic compounds that are known to have antioxidant properties.

Further embodiments of the compositions of the disclosure comprise a combination of ingredients such as microcrystalline wax, beeswax, *Butyrospermum parkii* (shea) butter (described above), and *Mangifera indica* (mango) seed butter.

Microcrystalline waxes are a type of wax produced by de-oiling petrolatum, as part of the petroleum refining process. In contrast to the more familiar paraffin wax which contains mostly unbranched alkanes, microcrystalline wax contains a higher percentage of isoparaffinic (branched) hydrocarbons and naphthenic hydrocarbons. It is characterized by the fineness of its crystals in contrast to the larger crystal of paraffin wax. It consists of high molecular weight saturated aliphatic hydrocarbons, and is generally darker, more viscous, denser, tackier and more elastic than paraffin waxes, and has a higher molecular weight and melting point. The elastic and adhesive characteristics of microcrystalline waxes are related to the non-straight chain components which they contain. Typical microcrystalline wax crystal structure is small and thin, making them more flexible than paraffin wax.

Beeswax (Cera alba) is a natural wax produced by honey bees of the genus *Apis*. Beeswax is a tough wax formed from a mixture of several compounds. Its main components are palmitate, palmitoleate, and oleate esters of long-chain (30-32 carbons) aliphatic alcohols, with the ratio of triacontanyl palmitate $CH_3(CH_2)_{29}O—CO—(CH_2)_{14}CH_3$ to cerotic acid $CH_3(CH_2)_{24}COOH$, the two principal components, being 6:1.

*Mangifera indica* is a species of mango in the Anacardiaceae family. Mango Butter has a high content of stearic acid. It has good emolliency and lends protection against the sun. It also prevents drying of the skin, the formation of wrinkles, reduces degeneration of skin cells, and restores cell elasticity.

The above compositions can be applied to the skin and remain on the skin for a period of time (e.g., at least 1, 2, 3, 4, 5, 10, 20, 30, or 60 minutes or more). After which, the composition, if needed, can be rinsed from the skin or peeled from the skin. Additionally, after removal of the composition, a moisturizer may be applied to the skin.

A. Amounts of Ingredients

It is contemplated that the compositions disclosed herein can include any amount of the ingredients discussed in this specification. The compositions can also include any number of combinations of additional ingredients described throughout this specification (e.g., pigments, or additional cosmetic or pharmaceutical ingredients). The concentrations of the any ingredient within the compositions can vary. In non-limiting embodiments, for example, the compositions can comprise, consisting essentially of, or consist of, in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.0550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or any range derivable therein, of at least one of the ingredients that are mentioned throughout the specification and claims. In non-limiting aspects, the percentage can be calculated by weight or volume of the total composition. A person of ordinary skill in the art would understand that the concentrations can vary depending on the addition, substitution, and/or subtraction of ingredients in a given composition.

B. Vehicles

The compositions disclosed herein can be incorporated into all types of vehicles. Non-limiting examples include emulsions (e.g., water-in-oil, water-in-oil-in-water, oil-in-water, silicone-in-water, water-in-silicone, oil-in-water-in-oil, oil-in-water-in-silicone emulsions), creams, lotions, solutions (both aqueous and hydro-alcoholic), anhydrous bases (such as lipsticks and powders), gels, masks, peels, and ointments. Variations and other appropriate vehicles will be apparent to the skilled artisan and are appropriate for use in the present invention. In certain aspects, it is important that the concentrations and combinations of the compounds, ingredients, and agents be selected in such a way that the combinations are chemically compatible and do not form complexes which precipitate from the finished product.

C. Additional Ingredients

In addition to the combination of ingredients disclosed by the inventors, the compositions can also include additional ingredients such as cosmetic ingredients and pharmaceutical active ingredients. Non-limiting examples of these additional ingredients are described in the following subsections.

1. Cosmetic Ingredients

The CTFA International Cosmetic Ingredient Dictionary and Handbook (2004 and 2008) describes a wide variety of non-limiting cosmetic ingredients that can be used in the compositions disclosed herein. Examples of these ingredient classes include: fragrances (artificial and natural; e.g., gluconic acid, phenoxyethanol, and triethanolamine), dyes and colorants (e.g., Blue 1, Blue 1 Lake, Red 40, Red 28 Lake, Red 7 Lake, Red 6 Lake, titanium dioxide, Unipure Red 6, Unipure Red 28, Unipure Red 33, Unipure Yellow OX, Unipure Yellow 5, FD&C blue 1, D&C blue no. 4, D&C green no. 5, D&C orange no. 4, D&C red no. 17, D&C red no. 6, D&C red no. 7, D&C red no. 30, D&C red no. 33, D&C violet no. 2, D&C yellow no. 10, D&C yellow no. 11, iron oxides, chromium oxides, tin oxide, ultramarines, and mica), flavoring agents/aroma agents (e.g., *Stevia rebaudiana* (sweetleaf) extract, and menthol), adsorbents, lubricants, solvents (e.g., water, hydrocarbons, hexylene glycol, isododecane, octyldodecanol, glycerin, and propylene glycol), moisturizers (including, e.g., emollients, humectants, film formers, occlusive agents, and agents that affect the natural moisturization mechanisms of the skin), water-repellants, UV absorbers (physical and chemical absorbers such as para-aminobenzoic acid ("PABA") and corresponding PABA derivatives, titanium dioxide, zinc oxide, etc.), essential oils, vitamins (e.g., A, B, C, D, E, and K), opacifying agents (e.g., styrene/butadiene copolymer), trace metals (e.g., zinc, calcium and selenium), inorganic salts (e.g., sodium chloride, magnesium nitrate, and magnesium chloride), anti-irritants (e.g., steroids and non-steroidal anti-inflammatories), botanical extracts (e.g., aloe vera, chamomile, cucumber extract, *ginkgo biloba, ginseng*, and rosemary), anti-microbial agents, antioxidants (e.g., BHT and tocopherol), chelating agents (e.g., caprylhydroxamic acid, disodium EDTA, and tetrasodium EDTA), preservatives (e.g., methylparaben and propylparaben), pH adjusters (e.g., sodium hydroxide, triethanolamine, and citric acid), absorbents (e.g., aluminum starch octenylsuccinate, kaolin, corn starch, oat starch, cyclodextrin, talc, silica, and zeolite), skin bleaching and lightening agents (e.g., hydroquinone and niacinamide lactate), humectants (e.g., sorbitol, urea, methyl gluceth-20, and mannitol), exfoliants, waterproofing agents (e.g., magnesium/aluminum hydroxide stearate), conditioning agents (e.g., aloe extracts, allantoin, bisabolol, ceramides, dimethicone, hyaluronic acid, biosaccharide gum-1, ethylhexylglycerin, pentylene glycol, hydrogenated polydecene, octyldodecyl oleate, and dipotassium glycyrrhizate), and film formers (e.g., acrylates copolymer and polyquarternium-7). Non-limiting examples of some of these ingredients are provided in the following subsections.

a. UV Absorption Agents

UV absorption agents that can be used in combination with the compositions disclosed herein include chemical and physical sunblocks. Non-limiting examples of chemical sunblocks that can be used include para-aminobenzoic acid (PABA), PABA esters (glyceryl PABA, amyldimethyl PABA and octyldimethyl PABA), butyl PABA, ethyl PABA, ethyl dihydroxypropyl PABA, benzophenones (oxybenzone, sulisobenzone, benzophenone, and benzophenone-1 through 12), cinnamates (octyl methoxycinnamate, isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (homomethyl salicylate, benzyl salicylate, glycol salicylate, isopropylbenzyl salicylate, etc.), anthranilates, ethyl urocanate, homosalate, octisalate, oxtinoxate, dibenzoylmethane derivatives (e.g., avobenzone), octocrylene, octyl triazone, digalloyl trioleate, glyceryl aminobenzoate, lawsone with dihydroxyacetone, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetramethylbutylphenol, and bis-ethylhexyloxyphenol methoxyphenyltriazine, 4-methylbenzylidene camphor, and isopentyl 4-methoxycinnamate. Non-limiting examples of physical sunblocks include, kaolin, talc, petrolatum and metal oxides (e.g., titanium dioxide and zinc oxide).

b. Moisturizing Agents

Non-limiting examples of moisturizing agents that can be used with the compositions disclosed herein include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrrolidone carboxylic acid, potassium PCA, propylene glycol, sodium glucuronate, sodium PCA, sorbitol, sucrose, trehalose, urea, and xylitol.

Other examples include acetylated lanolin, acetylated lanolin alcohol, alanine, algae extract, aloe barbadensis, aloe-barbadensis extract, aloe barbadensis gel, althea officinalis extract, apricot (prunus armeniaca) kernel oil, arginine, arginine aspartate, arnica montana extract, aspartic acid, avocado (persea gratissima) oil, barrier sphingolipids, butyl alcohol, beeswax, behenyl alcohol, beta-sitosterol, birch (betula alba) bark extract, borage (borago officinalis) extract, butcherbroom (ruscus aculeatus) extract, butylene glycol, calendula officinalis extract, calendula officinalis oil, candelilla (euphorbia cerifera) wax, canola oil, caprylic/capric triglyceride, cardamom (elettaria cardamomum) oil, carnauba (copernicia cerifera) wax, carrot (daucus carota sativa) oil, castor (ricinus communis) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (anthemis nobilis) oil, cholesterol, cholesterol esters, cholesteryl hydroxystearate, citric acid, clary (salvia sclarea) oil, cocoa (theobroma cacao) butter, coco-caprylate/caprate, coconut (cocos nucifera) oil, collagen, collagen amino acids, corn (zea mays)oil, fatty acids, decyl oleate, dimethicone copolyol, dimethiconol, dioctyl adipate, dioctyl succinate, dipentaerythrityl hexacaprylate/hexacaprate, DNA, erythritol, ethoxydiglycol, ethyl linoleate, eucalyptus globulus oil, evening primrose (oenothera biennis) oil, fatty acids, geranium maculatum oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (vitis vinifera) seed oil, hazel (corylus americana) nut oil, hazel (corylus avellana) nut oil, hexylene glycol, hyaluronic acid, hybrid safflower (carthamus tinctorius) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (jasminum officinale) oil, jojoba (buxus chinensis) oil, kelp, kukui (aleurites moluccana) nut oil, lactamide MEA, laneth-16, laneth-10 acetate, lanolin, lanolin acid, lanolin alcohol, lanolin oil, lanolin wax, lavender (lavandula angustifolia) oil, lecithin, lemon (citrus medica limonum) oil, linoleic acid, linolenic acid, macadamia ternifolia nut oil, maltitol, matricaria (chamomilla recutita) oil, methyl glucose sesquistearate, methylsilanol PCA, mineral oil, mink oil, mortierella oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (olea europaea) oil, orange (citrus aurantium dulcis) oil, palm (elaeis guineensis) oil, palmitic acid, pantethine, panthenol, panthenyl ethyl ether, paraffin, PCA, peach (prunus persica) kernel oil, peanut (arachis hypogaea) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG-40 sorbitan peroleate, PEG-5 soy sterol, PEG-10 soy sterol, PEG-2 stearate, PEG-8 stearate, PEG-20 stearate, PEG-32 stearate, PEG-40 stearate, PEG-50 stearate, PEG-100 stearate, PEG-150 stearate, pentadecalactone, peppermint (mentha piperita) oil, petrolatum, phospholipids, polyamino sugar condensate, polyglyceryl-3 diisostearate, polyquarternium-24, polysorbate 20, polysorbate 40, polysorbate 60, polysorbate 80, polysorbate 85, potassium myristate, potassium palmitate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, retinol, retinyl palmitate, rice (oryza sativa) bran oil, RNA, rosemary (rosmarinus officinalis) oil, rose oil, safflower (carthamus tinctorius) oil, sage (salvia officinalis) oil, sandalwood (santalum album) oil, serine, serum protein, sesame (sesamum indicum) oil, shea butter (butyrospermum parkii), silk powder, sodium chondroitin sulfate, sodium hyaluronate, sodium lactate, sodium palmitate, sodium PCA, sodium polyglutamate, soluble collagen, sorbitan laurate, sorbitan oleate, sorbitan palmitate, sorbitan sesquioleate, sorbitan stearate, sorbitol, soybean (glycine soja) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (helianthus annuus) seed oil, sweet almond (prunus amygdalus dulcis) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (triticum vulgare) germ oil, and ylang ylang (cananga odorata) oil c. Antioxidants Non-limiting examples of antioxidants that can be used with the compositions disclosed herein include acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thioglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

d. Structuring Agents

In other non-limiting aspects, the compositions disclosed herein can include a structuring agent. Structuring agent, in certain aspects, assist in providing rheological characteristics to the composition to contribute to the composition's stability. In other aspects, structuring agents can also function as an emollient, emulsifier or surfactant. Non-limiting examples of structuring agents include stearic acid, palmitic acid, stearyl alcohol, cetyl alcohol, PPG-30 cetyl ether, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, polyoxyethylene methylglucoside dioleate, tea-lauryl sulfate, polyethylene glycol ester of stearic acid, C12-15 alkyl benzoate, propylene glycol myristyl ether acetate, 3-hydroxypropyl (E)-octadec-9-enoate, sorbitan laurate, sorbitan stearate, carbomer, ammonium acryloyldimethyltaurate/carboxyethyl acrylate crosspolymer, sodium laureth sulfate, hydroxypropyl cyclodextrin, PPG-26 oleate, and mixtures thereof e. Emulsifiers In certain aspects disclosed herein, the compositions do not include an emulsifier. In other aspects, however, the compositions can include one or more emulsifiers. Emulsifiers can reduce the interfacial tension between phases and improve the formulation and stability of an emulsion. The emulsifiers can be nonionic, cationic, anionic, and zwitterionic emulsifiers (See McCutcheon's (1986); U.S. Pat. Nos. 5,011,681; 4,421,769; 3,755,560). Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, cetearyl glucoside, cetearyl alcohol, C12-13 pareth-3, PPG-2 methyl glucose ether distearate, PPG-5-ceteth-20, bis-PEG/PPG-20/20 dimethicone, sorbitan isostearate, ceteth-10, polysorbate 80, cetyl phosphate, potassium cetyl phosphate, diethanolamine cetyl phosphate, polysorbate 60, glyceryl stearate, PEG-100 stearate, arachidyl alcohol, arachidyl glucoside, C20-40 alcohols, and mixtures thereof.

f. Silicone Containing Compounds

In non-limiting aspects, silicone containing compounds include any member of a family of polymeric products whose molecular backbone is made up of alternating silicon and oxygen atoms with side groups attached to the silicon atoms. By varying the —Si—O— chain lengths, side groups, and crosslinking, silicones can be synthesized into a wide variety of materials. They can vary in consistency from liquid to gel to solids.

The silicone containing compounds that can be used in compositions disclosed herein include those described in this specification or those known to a person of ordinary skill in the art. Non-limiting examples include silicone oils (e.g., volatile and non-volatile oils), gels, and solids. In certain aspects, the silicon containing compounds includes a silicone oils such as a polyorganosiloxane. Non-limiting examples of polyorganosiloxanes include dimethicone, cyclomethicone, polysilicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e., normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e., dimethicones having a viscosity of about 50 cst or less (e.g., dimethicones such as Dow Corning 200-0.5 cst Fluid). The Dow Corning Fluids are available from Dow Corning Corporation, Midland, Mich. Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers end-blocked with trimethylsiloxy units, respectively. Silicone containing compounds of the invention may also be used as bulking agents (e.g., silicic acid and aluminum calcium sodium silicate). Other non-limiting volatile silicone oils that can be used in the compositions disclosed herein include those available from General Electric Co., Silicone Products Div., Waterford, N.Y. and SWS Silicones Div. of Stauffer Chemical Co., Adrian, Mich.

g. Essential Oils

Essential oils include oils derived from herbs, flowers, trees, and other plants. Such oils are typically present as tiny droplets between the plant's cells, and can be extracted by several methods known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 160° to 240° C. and densities ranging from about 0.759 to about 1.096.

Essential oils typically are named by the plant from which the oil is found. For example, rose oil or peppermint oil are derived from rose or peppermint plants, respectively. Non-limiting examples of essential oils that can be used in the compositions disclosed herein include sesame oil, macadamia nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, *eucalyptus* oil, fennel oil, sea fennel oil, frankincense oil, *geranium* oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang ylang. Other essential oils known to those of skill in the art are also contemplated as being useful within the compositions disclosed herein.

h. Thickening Agents

Thickening agents, including thickener or gelling agents, include substances which that can increase or control the viscosity of a composition. Thickeners includes those that can increase the viscosity of a composition without substantially modifying the efficacy of the active ingredient within the composition. Thickeners can also increase the stability of the compositions disclosed herein. In certain aspects disclosed herein, thickeners include hydrogenated polyisobutene, trihydroxystearin, ammonium acryloyldimethyltaurate/vp copolymer, or mixtures thereof.

Non-limiting examples of additional thickening agents that can be used in the compositions disclosed herein include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, Fourth edition, 1991, pp. 12 and 80). Examples of commercially available carboxylic acid polymers include carbomers, which are homopolymers of acrylic acid crosslinked with allyl ethers of sucrose or pentaerytritol (e.g., Carbopol™ 900 series from B. F. Goodrich).

Non-limiting examples of crosslinked polyacrylate polymers include cationic and nonionic polymers. Examples are described in U.S. Pat. Nos. 5,100,660; 4,849,484; 4,835,206; 4,628,078; 4,599,379.

Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a $C_{10}$-$C_{30}$ straight chain or branched chain alkyl group through an ether linkage. Typically these polymers are ethers of $C_{10}$-$C_{30}$ straight or branched chain alcohols with hydroxyalkylceluloses. Other useful polysaccharides include scleroglucans comprising a linear chain of (1-3) linked glucose units with a (1-6) linked glucose every three unit.

Non-limiting examples of gums that can be used with the present invention include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, *sclerotium* gum, sodium carboxymethyl dextran, sodium carrageenan, tragacanth gum, xanthan gum, and mixtures thereof.

Further non-limiting examples of thickening agents include carbomer, cetyl alcohol, ammonium acryloydimethyltaurate/VP copolymer, aluminum starch actenylsuccinate, cocamidopropyl betaine, PPG-2 hydroxyethyl coco/isostearamide, tin oxide, hexadecane copolymer, calcium aluminum borosilicate, alumina, calcium sodium borosilicate, aluminum calcium sodium silicate, synthetic fluorphlogopite, and disodium EDTA.

i. Preservatives

Non-limiting examples of preservatives that can be used in the composition disclosed herein include quaternary ammonium preservatives such as polyquarternium-1 and benzalkonium halides (e.g., benzalkonium chloride ("BAC") and benzalkonium bromide), parabens (e.g., methylparabens and propylparabens), phenoxyethanol, benzyl alcohol, chlorobutanol, phenol, sorbic acid, thimerosal, caprylyl glycol, iodopropynyl butylcarbamate, methylisothiazolinone, methylchloroisothiazolinone, sodium benzoate, dimethylol-5,5-dimethylhydantoin, 3-iodo-2-propynyl butyl carbamate, phenoxyethanol, caprylyl alcohol, ethylhexyl glycerin, hexylene glycol, DMDM hydantoin, chlorphenesin, and combinations thereof.

Conditioning Agents

Non-limiting examples of conditioning agents that can be used in the context of the present invention include caprylyl glycol, ethylhexylglycerin, PEG-12 dimethicone, hydroxypropyl cyclodextrin, dimethicone, tocopheryl acetate, *Butyrospermum parkii* (shea butter), polymers of polyethylene glycol and methicone, *Helianthus annuus* (sunflower) seed oil, PEG-18 glyceryl oleate/cocoate, cyclotetrasiloxane, cyclohexasiloxane, cyclopentasiloxane, tocopherol, glycerin, *Carthamus tinctorius* (safflower) oleosomes, butylene glycol, allantoin, hydrogenated palm kernel oil, caprylic/capric triglyceride, propylene glycol stearate, panthenol, polypropylene glycol ether of cetyl alcohol, polyquarternium-7, ethoxylated glyceryl esters, ethylhexyl palmitate. aloe extracts, bisabolol, ceramides, hyaluronic acid, dipotassium glycyrrhizate, cocamidopropyl betaine, pentaerythrityl tetraisostearate, glyceryl behenate/eicosadioate, tridecyl trimellitate, and mixtures thereof.

2. Pharmaceutical Ingredients

Pharmaceutical active agents are also contemplated as being useful with the compositions disclosed herein. Non-limiting examples of pharmaceutical active agents include anti-acne agents, agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antipsoriatic agents, antiseborrheic agents, biologically active proteins and peptides, burn treatment agents, cauterizing agents, depigmenting agents, depilatories, diaper rash treatment agents, enzymes, hair growth stimulants, hair growth retardants including DFMO and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, wound treatment agents, wound healing agents, etc.

D. Kits

Kits are also contemplated as being used in certain aspects disclosed herein. For instance, compositions disclosed herein can be included in a kit. A kit can include a container. Containers can include a bottle, a metal tube, a laminate tube, a plastic tube, a dispenser, a pressurized container, a barrier container, a package, a compartment, a lipstick container, a compact container, cosmetic pans that can hold cosmetic compositions, or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of the composition. In other embodiments, the container can be squeezed (e.g., metal, laminate, or plastic tube) to dispense a desired amount of the composition. The composition can be dispensed as a spray, an aerosol, a liquid, a fluid, or a semi-solid. The containers can have spray, pump, or squeeze mechanisms. A kit can also include instructions for employing the kit components as well the use of any other compositions included in the container. Instructions can include an explanation of how to apply, use, and maintain the compositions.

EXAMPLES

The following examples are included to demonstrate preferred embodiments of the invention. It should be appreciated by those of skill in the art that the techniques disclosed in the examples which follow represent techniques disclosed by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Formulations having the ingredients from Example 1 were prepared as topical skin compositions. The formulation in Table 1 was prepared as a lip mask. The formulation in Table 2 was prepared as a body buffing cream.

TABLE 1*

| Ingredient | % Concentration (by weight) |
| --- | --- |
| water | 73 |
| bentonite | 7 |
| glyceryl stearate | 3 |
| stearic acid | 2 |
| PEG-100 stearate | 2 |
| glycerin | 2 |
| hydrogenated polyisobutene | 1 |
| cetyl alcohol | 1 |
| PVP | 1 |
| petrolatum | 1 |
| cetyl esters | 1 |
| stearyl alcohol | 1 |
| sorbitol | 0.7 |
| triethanolamine | 0.6 |
| magnesium aluminum silicate | 0.5 |
| titanium dioxide | 0.5 |
| butylene glycol | 0.2 |
| hydroxyethylcellulose | 0.2 |
| methylparaben | 0.2 |
| DMDM hydantoin | 0.1 |
| tocopheryl acetate | 0.1 |
| flavoring agent / aroma gent | 0.1 |
| disodium EDTA | 0.1 |
| Camellia sinensis leaf extract | 0.02 |
| Excipients** and/or hydrated silica | q.s. |

*Formulation can be prepared by mixing the ingredients in a beaker under heat 70-75° C. until homogenous. Subsequently, the formulation can be cooled to standing room temperature (20-25° C.).
**Excipients were added to modify the rheological properties of the composition. Alternatively, the amount of water can be varied so long as the amount of water in the composition is at least 60% w/w, and preferably between 70 to 80% w/w.

TABLE 2*

| Ingredient | % Concentration (by weight) |
| --- | --- |
| water | 62 |
| disodium cocoamphodiacetate | 10 |
| glyceryl stearate | 7 |
| cetyl alcohol | 3 |
| PPG-5-ceteth-10 phosphate | 2 |
| sodium laureth sulfate | 1.5 |
| cocamidopropyl hydroxysultaine | 1.3 |
| sorbitol | 0.7 |
| fragrance/parfum agent | 0.5 |
| titanium dioxide | 0.5 |
| hydroxyethylcellulose | 0.5 |
| citric acid | 0.4 |
| sodium chloride | 0.3 |
| methylparaben | 0.2 |
| DMDM hydantoin | 0.1 |
| disodium EDTA | 0.1 |
| Excipients** and/or hydrated silica | q.s. |

*Formulation can be prepared by mixing the ingredients in a beaker under heat 70-75° C. until homogenous. Subsequently, the formulation can be cooled to standing room temperature (20-25° C.).
**Excipients were added to modify the rheological properties of the composition. Alternatively, the amount of water can be varied so long as the amount of water in the composition is at least 50% w/w, and preferably between 60 to 70% w/w.

TABLE 3*

| Ingredient** | % Concentration (by weight) |
| --- | --- |
| sucrose | 40 |
| tridecyl timellitate | 15 |
| Butyrospermum parkii (Shea) butter | 10 |
| glycerin | 9 |
| Helianthus annus (sunflower) seed oil | 9 |
| caprylic/capric triglyceride | 8 |
| trihydroxystearin | 4.5 |
| glyceryl stearate | 1.2 |
| excipients*** | q.s. |

*Formulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition.
**Any of the additional ingredients (or combination thereof) described in the specification can be used.
***Excipients can be added, for example, to modify the rheological properties of the composition.

TABLE 4*

| Ingredient** | % Concentration (by weight) |
| --- | --- |
| caprylic/capric triglyceride | 29 |
| tridecyl trimellitate | 17 |
| jojoba esters | 12 |
| Helianthus annus (sunflower) seed oil | 9 |
| microcrystalline wax | 7 |
| beeswax | 7 |
| glyceryl stearate | 5 |
| cetyl alcohol | 4 |
| pentaerythrityl tetraisostearate | 4 |
| Butyrospermum parkii (shea) butter | 1 |
| Mangifera indica (mango) seed butter | 1 |
| excipients*** | q.s. |

*Formulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition.
**Any of the additional ingredients (or combination thereof) described in the specification can be used.
***Excipients can be added, for example, to modify the rheological properties of the composition.

TABLE 5*

| Ingredient** | % Concentration (by weight) |
|---|---|
| caprylic/capric triglyceride | 23 |
| tridecyl trimellitate | 17 |
| jojoba esters | 3 |
| *Helianthus annus* (sunflower) seed oil | 8 |
| microcrystalline wax | 7 |
| beeswax | 5 |
| glyceryl stearate | 5 |
| cetyl alcohol | 4 |
| pentaerythrityl tetraisostearate | 4 |
| *Butyrospermum parkii* (shea) butter | 10 |
| *Mangifera indica* (mango) seed butter | 9 |
| excipients*** | q.s. |

*Formulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition.
**Any of the additional ingredients (or combination thereof) described in the specification can be used.
***Excipients can be added, for example, to modify the rheological properties of the composition.

TABLE 6*

| Ingredient | % Concentration (by weight) |
|---|---|
| water | 71 |
| isodecane | 6 |
| caprylic/capric triglyceride | 2 |
| dimethicone | 2 |
| cetyl alcohol | 1.5 |
| stearic acid | 1 |
| arachidyl alcohol | 1 |
| hydroxyethyl acrylate/sodium acryloyldimethyl taurate copolymer | 0.5 |
| behenyl alcohol | 0.5 |
| isohexadecane | 0.5 |
| arachidyl glucoside | 0.2 |
| acrylates/$C_{10-30}$ alkyl acrylate crosspolymer | 0.2 |
| polysorbate 60 | 0.1 |
| Excipients** | q.s. |

*Formulation can be prepared by mixing the ingredients in a beaker under heat 70-75° C. until homogenous. Subsequently, the formulation can be cooled to standing room temperature (20-25° C.).
**Excipients were added to modify the rheological properties of the composition. Alternatively, the amount of water can be varied so long as the amount of water in the composition is at least 60% w/w, and preferably between 70 to 80% w/w.

Example 2

Additional Assays

Additional assays that can be used to determine the efficacy of any one of the ingredients or any combination of ingredients or compositions having said combination of ingredients disclosed throughout the specification and claims can be determined by methods known to those of ordinary skill in the art. The following are non-limiting assays that can be used in the context of the present invention. It should be recognized that other testing procedures can be used, including, for example, objective and subjective procedures.

B16 Pigmentation Assay:

Melanogenesis is the process by which melanocytes produce melanin, a naturally produced pigment that imparts color to skin, hair, and eyes. Inhibiting melanogenesis is beneficial to prevent skin darkening and lighten dark spots associated with aging. This bioassay utilizes B16-F1 melanocytes (ATCC), an immortalized mouse melanoma cell line, to analyze the effect of compounds on melanogenesis. The endpoint of this assay is a spectrophotometric measurement of melanin production and cellular viability. B16-F1 melanocytes, can be cultivated in standard DMEM growth medium with 10% fetal bovine serum (Mediatech) at 37° C. in 10% $CO_2$ and then treated with any one of the active ingredients, combination of ingredients, or compositions having said combinations disclosed in the specification for 6 days. Following incubation, melanin secretion was measured by absorbance at 405 nm and cellular viability was quantified.

Collagen Stimulation Assay:

Collagen is an extracellular matrix protein critical for skin structure. Increased synthesis of collagen helps improve skin firmness and elasticity. This bioassay can be used to examine the effect of any one of the active ingredients, combination of ingredients, or compositions having said combinations disclosed in the specification on the production of procollagen peptide (a precursor to collagen) by human epidermal fibroblasts. The endpoint of this assay is a spectrophotometric measurement that reflects the presence of procollagen peptide and cellular viability. The assay employs the quantitative sandwich enzyme immunoassay technique whereby a monoclonal antibody specific for procollagen peptide has been pre-coated onto a microplate. Standards and samples can be pipetted into the wells and any procollagen peptide present is bound by the immobilized antibody. After washing away any unbound substances, an enzyme-linked polyclonal antibody specific for procollagen peptide can be added to the wells. Following a wash to remove any unbound antibody-enzyme reagent, a substrate solution can be added to the wells and color develops in proportion to the amount of procollagen peptide bound in the initial step using a microplate reader for detection at 450 nm. The color development can be stopped and the intensity of the color can be measured. Subconfluent normal human adult epidermal fibroblasts (Cascade Biologics) cultivated in standard DMEM growth medium with 10% fetal bovine serum (Mediatech) at 37° C. in 10% $CO_2$, can be treated with each of the combination of ingredients or compositions having said combinations disclosed in the specification for 3 days. Following incubation, cell culture medium can be collected and the amount of procollagen peptide secretion quantified using a sandwich enzyme linked immuno-sorbant assay (ELISA) from Takara (#MK101).

Tumor Necrosis Factor Alpha (TNF-α) Assay:

The prototype ligand of the TNF superfamily, TNF-α, is a pleiotropic cytokine that plays a central role in inflammation. Increase in its expression is associated with an up regulation in pro-inflammatory activity. This bioassay can be used to analyze the effect of any one of the active ingredients, combination of ingredients, or compositions having said combinations disclosed in the specification on the production of TNF-α by human epidermal keratinocytes. The endpoint of this assay can be a spectrophotometric measurement that reflects the presence of TNF-α and cellular viability. The assay employs the quantitative sandwich enzyme immunoassay technique whereby a monoclonal antibody specific for TNF-α has been pre-coated onto a microplate. Standards and samples can be pipetted into the wells and any TNF-α present is bound by the immobilized antibody. After washing away any unbound substances, an enzyme-linked polyclonal antibody specific for TNF-α can be added to the wells. Following a wash to remove any unbound antibody-enzyme reagent, a substrate solution can be added to the wells and color develops in proportion to the amount of TNF-α bound in the initial step using a microplate reader for detection at 450 nm. The color development can be stopped and the intensity of the color can be measured.

Subconfluent normal human adult keratinocytes (Cascade Biologics) cultivated in EpiLife standard growth medium (Cascade Biologics) at 37° C. in 5% $CO_2$, can be treated with phorbol 12-myristate 13-acetate (PMA, 10 ng/ml, Sigma Chemical, #P1585-1MG) and any one of the active ingredients, combination of ingredients, or compositions having said combinations disclosed in the specification for 6 hours. PMA has been shown to cause a dramatic increase in TNF-α secretion which peaks at 6 hours after treatment. Following incubation, cell culture medium can be collected and the amount of TNF-α secretion quantified using a sandwich enzyme linked immuno-sorbant assay (ELISA) from R&D Systems (#DTA00C).

Antioxidant (AO) Assay:

An in vitro bioassay that measures the total anti-oxidant capacity of any one of the ingredients, combination of ingredients, or compositions having said combinations disclosed in the specification. The assay relies on the ability of antioxidants in the sample to inhibit the oxidation of ABTS® (2,2'-azino-di-[3-ethylbenzthiazoline sulphonate]) to ABTS®•+ by metmyoglobin. The antioxidant system of living organisms includes enzymes such as superoxide dismutase, catalase, and glutathione peroxidase; macromolecules such as albumin, ceruloplasmin, and ferritin; and an array of small molecules, including ascorbic acid, α-tocopherol, β-carotene, reduced glutathione, uric acid, and bilirubin. The sum of endogenous and food-derived antioxidants represents the total antioxidant activity of the extracellular fluid. Cooperation of all the different antioxidants provides greater protection against attack by reactive oxygen or nitrogen radicals, than any single compound alone. Thus, the overall antioxidant capacity may give more relevant biological information compared to that obtained by the measurement of individual components, as it considers the cumulative effect of all antioxidants present in plasma and body fluids. The capacity of the antioxidants in the sample to prevent ABTS oxidation is compared with that of Trolox, a water-soluble tocopherol analogue, and is quantified as molar Trolox equivalents. Anti-Oxidant capacity kit #709001 from Cayman Chemical (Ann Arbor, Mich. USA) can be used as an in vitro bioassay to measure the total anti-oxidant capacity of each of any one of the active ingredients, combination of ingredients, or compositions having said combinations disclosed in the specification. The protocol can be followed according to manufacturer recommendations. The assay relied on antioxidants in the sample to inhibit the oxidation of ABTS® (2,2'-azino-di-[3-ethyl-benzthiazoline sulphonate]) to ABTS®•+ by metmyoglobin. The capacity of the antioxidants in the sample to prevent ABTS oxidation can be compared with that Trolox, a water-soluble tocopherol analogue, and was quantified as a molar Trolox equivalent.

ORAC Assay:

Oxygen Radical Absorption (or Absorbance) Capacity (ORAC) of any one of the active ingredients, combination of ingredients, or compositions having said combinations disclosed in the specification can also be assayed by measuring the antioxidant activity of such ingredients or compositions. This assay can quantify the degree and length of time it takes to inhibit the action of an oxidizing agent such as oxygen radicals that are known to cause damage cells (e.g., skin cells). The ORAC value of any one of the active ingredients, combination of ingredients, or compositions having said combinations disclosed in the specification can be determined by methods known to those of ordinary skill in the art (see U.S. Publication Nos. 2004/0109905 and 2005/0163880; Cao et al. (1993)), all of which are incorporated by reference). In summary, the assay described in Cao et al. (1993) measures the ability of antioxidant compounds in test materials to inhibit the decline of B-phycoerythrm (B-PE) fluorescence that is induced by a peroxyl radical generator, AAPH.

Mushroom Tyrosinase Activity Assay:

In mammalian cells, tyrosinase catalyzes two steps in the multi-step biosynthesis of melanin pigments from tyrosine (and from the polymerization of dopachrome). Tyrosinase is localized in melanocytes and produces melanin (aromatic quinone compounds) that imparts color to skin, hair, and eyes. Purified mushroom tyrosinase (Sigma) can be incubated with its substrate L-Dopa (Fisher) in the presence or absence of each of the active ingredients, any one of the combination of ingredients, or compositions having said combinations disclosed in the specification. Pigment formation can be evaluated by colorimetric plate reading at 490 nm. The percent inhibition of mushroom tyrosinase activity can be calculated compared to non-treated controls to determine the ability of test ingredients or combinations thereof to inhibit the activity of purified enzyme. Test extract inhibition was compared with that of kojic acid (Sigma).

Matrix Metalloproteinase Enzyme Activity (MMP3; MMP9) Assay:

An in vitro matrix metalloprotease (MMP) inhibition assay. MMPs are extracellular proteases that play a role in many normal and disease states by virtue of their broad substrate specificity. MMP3 substrates include collagens, fibronectins, and laminin; while MMP9 substrates include collagen VII, fibronectins and laminin. Using Colorimetric Drug Discovery kits from BioMol International for MMP3 (AK-400) and MMP-9 (AK-410), this assay is designed to measure protease activity of MMPs using a thiopeptide as a chromogenic substrate (Ac-PLG-[2 -mercapto-4-methyl-pentanoyl]-LG-OC2H5)5,6. The MMP cleavage site peptide bond is replaced by a thioester bond in the thiopeptide. Hydrolysis of this bond by an MMP produces a sulfhydryl group, which reacts with DTNB [5,5'-dithiobis(2-nitrobenzoic acid), Ellman's reagent] to form 2-nitro-5-thiobenzoic acid, which can be detected by its absorbance at 412 nm (c=13,600 M−1 cm−1 at pH 6.0 and above 7). The active ingredients, any one of the combination of ingredients, or compositions having said combinations disclosed in the specification can be assayed.

Cyclooxygenase (COX) Assay:

An in vitro cyclooxygenase-1 and -2 (COX-1, -2) inhibition assay. COX is a bifunctional enzyme exhibiting both cyclooxygenase and peroxidase activities. The cyclooxygenase activity converts arachidonic acid to a hydroperoxy endoperoxide (Prostaglandin G2; PGG2) and the peroxidase component reduces the endoperoxide (Prostaglandin H2; PGH2) to the corresponding alcohol, the precursor of prostaglandins, thromboxanes, and prostacyclins. This COX Inhibitor screening assay measures the peroxidase component of cyclooxygenases. The peroxidase activity is assayed colorimetrically by monitoring the appearance of oxidized N,N,N',N'-tetramethyl-p-phenylenediamine (TMPD). This inhibitor screening assay includes both COX-1 and COX-2 enzymes in order to screen isozyme-specific inhibitors. The Colormetric COX (ovine) Inhibitor screening assay (#760111, Cayman Chemical) can be used to analyze the effects of each of the active ingredients, any one of the combination of ingredients, or compositions having said combinations disclosed in the specification on the activity of purified cyclooxygnase enzyme (COX-1 or COX-2). According to manufacturer instructions, purified enzyme, heme and test extracts can be mixed in assay buffer and incubated with shaking for 15 min at room temperature. Following incubation, arachidonic acid and colorimetric substrate can be added to initiate the reaction. Color progression can be evaluated by colorimetric plate reading at 590 nm. The percent inhibition of COX-1 or COX-2 activity can be calculated compared to non-treated controls to determine the ability of test extracts to inhibit the activity of purified enzyme.

Lipoxygenase (LO) Assay:

An in vitro lipoxygenase (LO) inhibition assay. LOs are non-heme iron-containing dioxygenases that catalyze the addition of molecular oxygen to fatty acids. Linoleate and arachidonate are the main substrates for LOs in plants and animals. Arachadonic acid may then be converted to hydroxyeicosotrienenoic (HETE) acid derivatives, that are subsequently converted to leukotirenes, potent inflammatory mediators. This assay provides an accurate and convenient method for screening lipoxygenase inhibitors by measuring the hydroperoxides generated from the incubation of a lipoxygenase (5-, 12-, or 15-LO) with arachidonic acid. The Colorimetric LO Inhibitor screening kit (#760700, Cayman Chemical) can be used to determine the ability of each of the active ingredients, any one of the combination of ingredients, or compositions having said combinations disclosed in the specification to inhibit enzyme activity. Purified 15-lipoxygenase and test ingredients can be mixed in assay buffer and incubated with shaking for 10 min at room temperature. Following incubation, arachidonic acid can be added to initiate the reaction and mixtures incubated for an additional 10 min at room temperature. Colorimetric substrate can be added to terminate catalysis and color progression was evaluated by fluorescence plate reading at 490 nm. The percent inhibition of lipoxyganse activity can be calculated compared to non-treated controls to determine the ability of each of the active ingredients, any one of the combination of ingredients, or compositions having said combinations disclosed in the specification to inhibit the activity of purified enzyme.

Elastase Assay:

EnzChek® Elastase Assay (Kit# E-12056) from Molecular Probes (Eugene, Oreg. USA) can be used as an in vitro enzyme inhibition assay for measuring inhibition of elastase activity for each of the active ingredients, any one of the combination of ingredients, or compositions having said combinations disclosed in the specification. The EnzChek kit contains soluble bovine neck ligament elastin that can be labeled with dye such that the conjugate's fluorescence can be quenched. The non-fluorescent substrate can be digested by elastase or other proteases to yield highly fluorescent fragments. The resulting increase in fluorescence can be monitored with a fluorescence microplate reader. Digestion products from the elastin substrate have absorption maxima at ~505 nm and fluorescence emission maxima at ~515 nm. The peptide, chloromethyl ketone, can be used as a selective, collective inhibitor of elastase when utilizing the EnzChek Elastase Assay Kit for screening for elastase inhibitors.

Oil Control Assay:

An assay to measure reduction of sebum secretion from sebaceous glands and/or reduction of sebum production from sebaceous glands can be assayed by using standard techniques known to those having ordinary skill in the art. In one instance, the forehead can be used. Each of the active ingredients, any one of the combination of ingredients, or compositions having said combinations disclosed in the specification can be applied to one portion of the forehead once or twice daily for a set period of days (e.g., 1, 2, 3, 4, 5, 6, 7, 8, 9, 10, 11, 12, 13, 14, or more days), while another portion of the forehead is not treated with the composition. After the set period of days expires, then sebum secretion can be assayed by application of fine blotting paper to the treated and untreated forehead skin. This is done by first removing any sebum from the treated and untreated areas with moist and dry cloths. Blotting paper can then be applied to the treated and untreated areas of the forehead, and an elastic band can be placed around the forehead to gently press the blotting paper onto the skin. After 2 hours the blotting papers can be removed, allowed to dry and then transilluminated. Darker blotting paper correlates with more sebum secretion (or lighter blotting paper correlates with reduced sebum secretion.

Erythema Assay:

An assay to measure the reduction of skin redness can be evaluated using a Minolta Chromometer. Skin erythema may be induced by applying a 0.2% solution of sodium dodecyl sulfate on the forearm of a subject. The area is protected by an occlusive patch for 24 hrs. After 24 hrs, the patch is removed and the irritation-induced redness can be assessed using the a* values of the Minolta Chroma Meter. The a* value measures changes in skin color in the red region. Immediately after reading, the area is treated with the active ingredients, any one of the combination of ingredients, or compositions having said combinations disclosed in the specification. Repeat measurements can be taken at regular intervals to determine the formula's ability to reduce redness and irritation.

Skin Moisture/Hydration Assay:

Skin moisture/hydration benefits can be measured by using impedance measurements with the Nova Dermal Phase Meter. The impedance meter measures changes in skin moisture content. The outer layer of the skin has distinct electrical properties. When skin is dry it conducts electricity very poorly. As it becomes more hydrated increasing conductivity results. Consequently, changes in skin impedance (related to conductivity) can be used to assess changes in skin hydration. The unit can be calibrated according to instrument instructions for each testing day. A notation of temperature and relative humidity can also be made. Subjects can be evaluated as follows: prior to measurement they can equilibrate in a room with defined humidity (e.g., 30-50%) and temperature (e.g., 68-72° C.). Three separate impedance readings can be taken on each side of the face, recorded, and averaged. The T5 setting can be used on the impedance meter which averages the impedance values of every five seconds application to the face. Changes can be reported with statistical variance and significance. Each of the active ingredients, any one of the combination of ingredients, or compositions having said combinations disclosed in the specification can be assayed according to this process.

Skin Clarity and Reduction in Freckles and Age Spots Assay:

Skin clarity and the reduction in freckles and age spots can be evaluated using a Minolta Chromometer. Changes in skin color can be assessed to determine irritation potential due to product treatment using the a* values of the Minolta Chroma Meter. The a* value measures changes in skin color in the red region. This is used to determine whether each of the active ingredients, any one of the combination of ingredients, or compositions having said combinations disclosed in the specification is inducing irritation. The measurements can be made on each side of the face and averaged, as left and right facial values. Skin clarity can also be measured using the Minolta Meter. The measurement is a combination of the a*, b, and L values of the Minolta Meter and is related to skin brightness, and correlates well with skin smoothness and hydration. Skin reading is taken as above. In one non-limiting aspect, skin clarity can be described as L/C where C is chroma and is defined as $(a^2+b^2)^{1/2}$.

Skin Dryness, Surface Fine Lines, Skin Smoothness, and Skin Tone Assay:

Skin dryness, surface fine lines, skin smoothness, and skin tone can be evaluated with clinical grading techniques. For example, clinical grading of skin dryness can be determined by a five point standard Kligman Scale: (0) skin is soft and moist; (1) skin appears normal with no visible dryness; (2) skin feels slightly dry to the touch with no visible flaking; (3) skin feels dry, tough, and has a whitish appearance with some scaling; and (4) skin feels very dry, rough, and has a whitish appearance with scaling. Evaluations can be made independently by two clinicians and averaged.

Clinical Grading of Skin Tone Assay:

Clinical grading of skin tone can be performed via a ten point analog numerical scale: (10) even skin of uniform, pinkish brown color. No dark, erythremic, or scaly patches upon examination with a hand held magnifying lens. Microtexture of the skin very uniform upon touch; (7) even skin tone observed without magnification. No scaly areas, but slight discolorations either due to pigmentation or erythema. No discolorations more than 1 cm in diameter; (4) both skin discoloration and uneven texture easily noticeable. Slight scaliness. Skin rough to the touch in some areas; and (1) uneven skin coloration and texture. Numerous areas of scaliness and discoloration, either hypopigmented, erythremic or dark spots. Large areas of uneven color more than 1 cm in diameter. Evaluations were made independently by two clinicians and averaged.

Clinical Grading of Skin Smoothness Assay:

Clinical grading of skin smoothness can be analyzed via a ten point analog numerical scale: (10) smooth, skin is moist and glistening, no resistance upon dragging finger across surface; (7) somewhat smooth, slight resistance; (4) rough, visibly altered, friction upon rubbing; and (1) rough, flaky, uneven surface. Evaluations were made independently by two clinicians and averaged.

Skin Smoothness and Wrinkle Reduction Assay with Methods Disclosed in Packman et al.

(1978): Skin smoothness and wrinkle reduction can also be assessed visually by using the methods disclosed in Packman et al. (1978). For example, at each subject visit, the depth, shallowness and the total number of superficial facial lines (SFLs) of each subject can be carefully scored and recorded. A numerical score was obtained by multiplying a number factor times a depth/width/length factor. Scores are obtained for the eye area and mouth area (left and right sides) and added together as the total wrinkle score.

Skin Firmness Assay with a Hargens Ballistometer:

Skin firmness can be measured using a Hargens ballistometer, a device that evaluates the elasticity and firmness of the skin by dropping a small body onto the skin and recording its first two rebound peaks. The ballistometry is a small lightweight probe with a relatively blunt tip (4 square mm-contact area) was used. The probe penetrates slightly into the skin and results in measurements that are dependent upon the properties of the outer layers of the skin, including the stratum corneum and outer epidermis and some of the dermal layers.

Skin Softness/Suppleness Assay with a Gas Bearing Electrodynamometer:

Skin softness/suppleness can be evaluated using the Gas Bearing Electrodynamometer, an instrument that measures the stress/strain properties of the skin. The viscoelastic properties of skin correlate with skin moisturization. Measurements can be obtained on the predetermined site on the cheek area by attaching the probe to the skin surface with double-stick tape. A force of approximately 3.5 gm can be applied parallel to the skin surface and the skin displacement is accurately measured. Skin suppleness can then be calculated and is expressed as DSR (Dynamic Spring Rate in gm/mm).

Appearance of Lines and Wrinkles Assay with Replicas:

The appearance of lines and wrinkles on the skin can be evaluated using replicas, which is the impression of the skin's surface. Silicone rubber like material can be used. The replica can be analyzed by image analysis. Changes in the visibility of lines and wrinkles can be objectively quantified via the taking of silicon replicas form the subjects' face and analyzing the replicas image using a computer image analysis system. Replicas can be taken from the eye area and the neck area, and photographed with a digital camera using a low angle incidence lighting. The digital images can be analyzed with an image processing program and are of the replicas covered by wrinkles or fine lines was determined.

Surface Contour of the Skin Assay with a Profilometer/Stylus Method:

The surface contour of the skin can be measured by using the profilometer/Stylus method. This includes either shining a light or dragging a stylus across the replica surface. The vertical displacement of the stylus can be fed into a computer via a distance transducer, and after scanning a fixed length of replica a cross-sectional analysis of skin profile can be generated as a two-dimensional curve. This scan can be repeated any number of times along a fix axis to generate a simulated 3-D picture of the skin. Ten random sections of the replicas using the stylus technique can be obtained and combined to generate average values. The values of interest include Ra which is the arithmetic mean of all roughness (height) values computed by integrating the profile height relative to the mean profile height. Rt which is the maximum vertical distance between the highest peak and lowest trough, and Rz which is the mean peak amplitude minus the mean peak height. Values are given as a calibrated value in mm. Equipment should be standardized prior to each use by scanning metal standards of know values. Ra Value can be computed by the following equation: $R_a$=Standardize roughness; $l_m$=the traverse (scan) length; and y=the absolute value of the location of the profile relative to the mean profile height (x-axis).

MELANODERM™ Assay:

In other non-limiting aspects, the efficacy of each of the active ingredients, any one of the combination of ingredients, or compositions having said combinations disclosed in the specification compositions can be evaluated by using a skin analog, such as, for example, MELANODERM™. Melanocytes, one of the cells in the skin analog, stain positively when exposed to L-dihydroxyphenyl alanine (L-DOPA), a precursor of melanin. The skin analog, MELANODERM™, can be treated with a variety of bases containing each of the active ingredients, any one of the combination of ingredients, or compositions having said combinations disclosed in the specification or with the base alone as a control. Alternatively, an untreated sample of the skin analog can be used as a control.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:

1. An anhydrous lip moisturizing composition comprising:
   12% to 22% by weight of tridecyl trimellitate;
   2% to 20% by weight of microcrystalline wax;
   1% to 15% by weight of jojoba esters;
   5% to 10% by weight of *Helianihus annus* (sunflower) seed oil;
   2% to 15% by weight of pentaerythrityl tetraisostearate;
   2% to 10% by weight of beeswax;
   0.01% to 2% by weight of *Biluyrospernuim parkii* (shea) butter; and
   0.01% to 2% by weight of *Mangifera indicas* (mango) seed butter.

2. The anhydrous lip moisturizing composition of claim 1, further comprising:
   silica;
   *Stevia rebaudiana* extract; and
   tocopheryl acetate.

3. A method of moisturizing lips, the method comprising applying the anhydrous lip moisturizing composition of claim 1 to the lips of a person, wherein the composition moisturizes the lips.

* * * * *